(12) United States Patent
Thakur et al.

(10) Patent No.: US 11,530,403 B2
(45) Date of Patent: Dec. 20, 2022

(54) RAPID AND EFFICIENT DE-GLYCOSYLATION OF GLYCOPROTEINS

(71) Applicant: Biocon Limited, Electronic City P.O. (IN)

(72) Inventors: Anushikha Thakur, Electronic City phase-1 (IN); Seija Rohil, Viveknagar post (IN); Shrivardhan Patil, Kolhapur (IN); Meenakshi Sudhakaran, Kochi (IN); Laxmi Adhikary, Bangalore (IN)

(73) Assignee: BIOCON LIMITED, Electronic City (IN)

( * ) Notice: Subject to any disclaimer, the term of this patent is extended or adjusted under 35 U.S.C. 154(b) by 0 days.

(21) Appl. No.: 16/462,085

(22) PCT Filed: Nov. 17, 2017

(86) PCT No.: PCT/IB2017/057205
§ 371 (c)(1),
(2) Date: May 17, 2019

(87) PCT Pub. No.: WO2018/092078
PCT Pub. Date: May 24, 2018

(65) Prior Publication Data
US 2020/0291377 A1 Sep. 17, 2020

(30) Foreign Application Priority Data
Nov. 18, 2016 (IN) .............................. 201641039420

(51) Int. Cl.
*C12N 9/80* (2006.01)
*C07K 1/16* (2006.01)
*C07K 14/47* (2006.01)
*G01N 27/447* (2006.01)

(52) U.S. Cl.
CPC .................. *C12N 9/80* (2013.01); *C07K 1/16* (2013.01); *C07K 14/473* (2013.01); *G01N 27/44791* (2013.01); *C07K 2317/41* (2013.01)

(58) Field of Classification Search
CPC ....................................................... C12N 9/80
See application file for complete search history.

(56) References Cited

U.S. PATENT DOCUMENTS

| | | | | |
|---|---|---|---|---|
| 7,265,084 B2 * | 9/2007 | DeFrees | ................. | C07K 1/006 514/1.3 |
| 8,119,357 B2 * | 2/2012 | Amor | ................. | G01N 33/5308 435/7.1 |
| 8,540,992 B2 * | 9/2013 | Naso | ....................... | A61P 29/00 424/141.1 |
| 9,856,502 B2 * | 1/2018 | Nair | ....................... | A61P 31/18 |

OTHER PUBLICATIONS

Freeze et al. 2010; Endoglycosidase and glycoamidase released of N-linked glycans. Current Protocols in Molecular Biology. 89(1): 17.13A1-17.13A.25.*
Masuda et al. 2015; Mass production of an active peptide-N-Glycosidase F using silkworm-baculovirus expression system. Mol. Biotechnol. 57: 735-745.*
Szabo, Z., et al. "Rapid release of N-linked glycans from glycoproteins by pressure-cycling technology." Analytical chemistry 82(6), 2010: 2588-2593.
Papac, Damon I., et al. "A high-throughput microscale method to release N-linked oligosaccharides from glycoproteins for matrix-assisted laser desorption/ionization time-of-flight mass spectrometric analysis." Glycobiology 8(5), 1998: 445-454.
International Search Report for International ApplicationNo. PCT/IB2017/057205, dated Feb. 23, 2018.

* cited by examiner

*Primary Examiner* — Karen Cochrane Carlson
(74) *Attorney, Agent, or Firm* — Katten Muchin Rosenman LLP

(57) ABSTRACT

The present invention discloses rapid and cost-effective method of de-glycosyation of a glycoprotein, wherein, glycoprotein is combined with anionic surfactant and reducing agent and non-ionic surfactant in order to obtain stable denatured glycoprotein. An endoglycosidase is further added to denatured glycoprotein to cleave N-linked glycans in order to obtain de-glycosylated protein. A rapid tool for assessing the protein conformation by partial de-glycosylation is also presented wherein the partial de-glycosylated protein is analysed using capillary electrophoresis (CE-SDS).

17 Claims, 10 Drawing Sheets

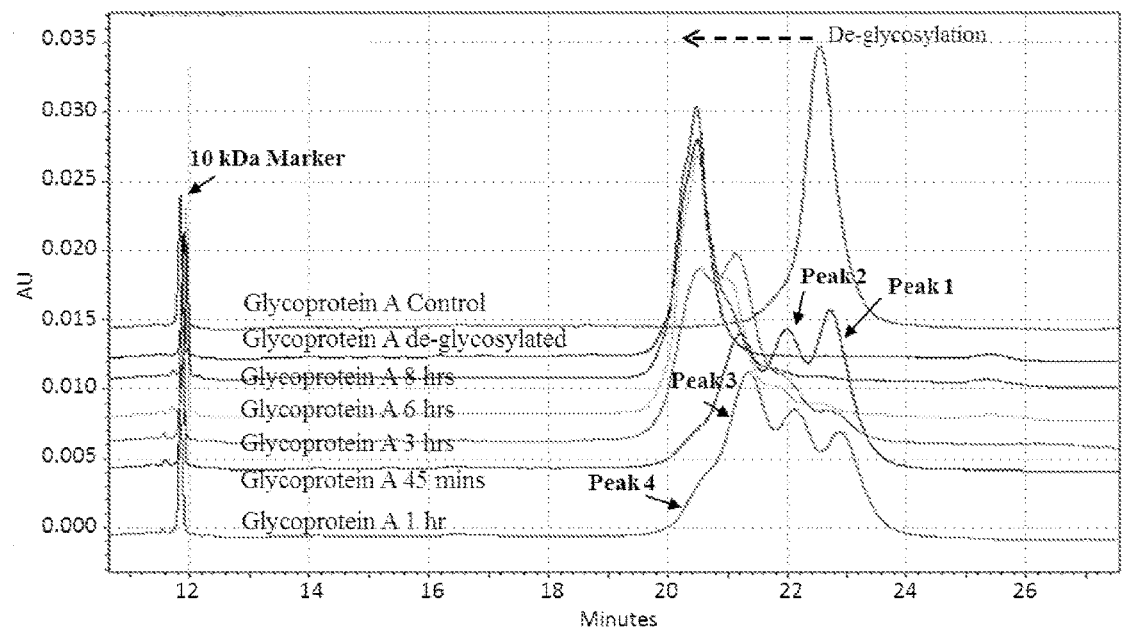
FIGURE 1 – Reduced CE-SDS profile of time course of partially de-glycosylated glycoprotein A
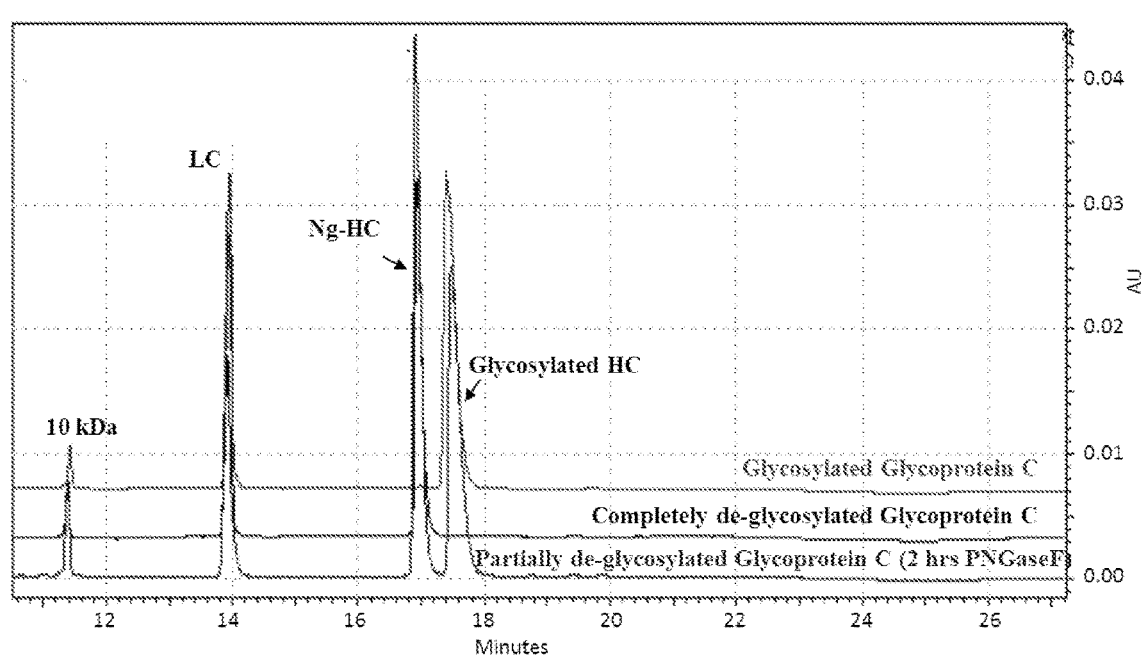
FIGURE 2 - Reduced CE-SDS profile of partially de-glycosylated glycoprotein C

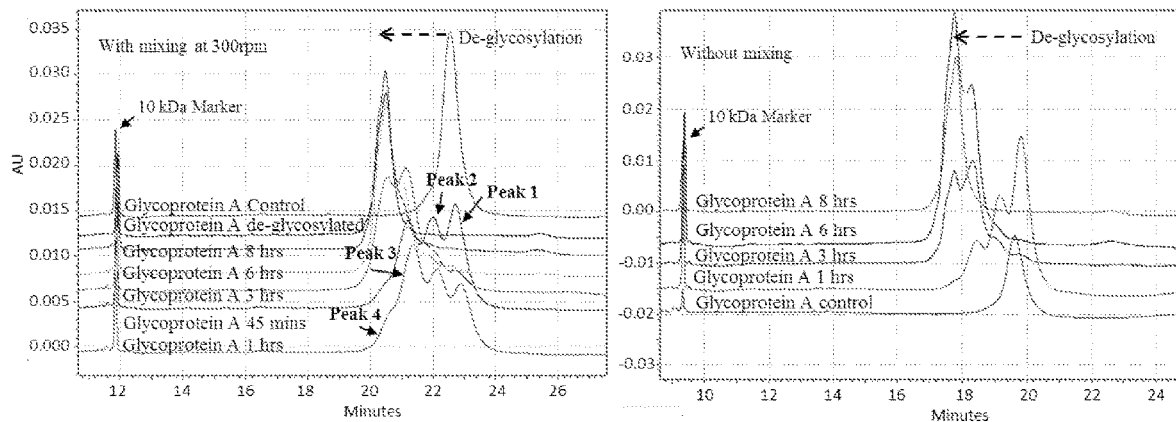
FIGURE 3 - Reduced CE-SDS profile of time course of partially de-glycosylated glycoprotein A with or without mixing.
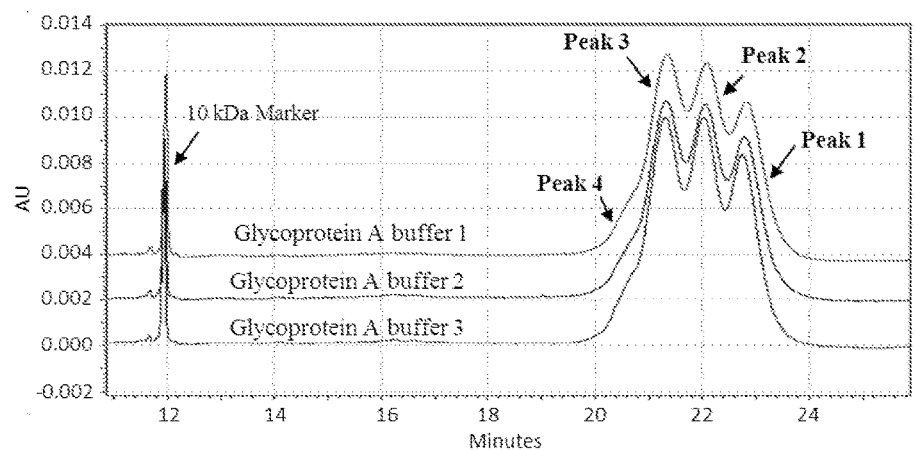
FIGURE 4 - Reduced CE-SDS profile of partially de-glycosylated glycoprotein A under different buffer formulations.

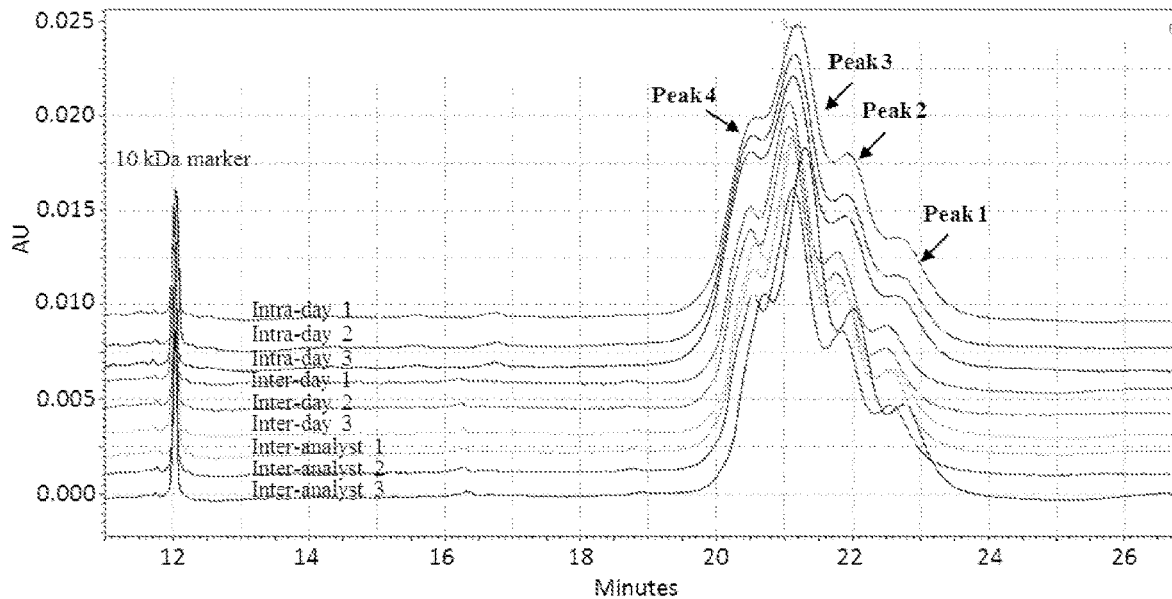
FIGURE 5 - Reduced CE-SDS profile of partially de-glycosylated glycoprotein A demonstrating intermediate precision.
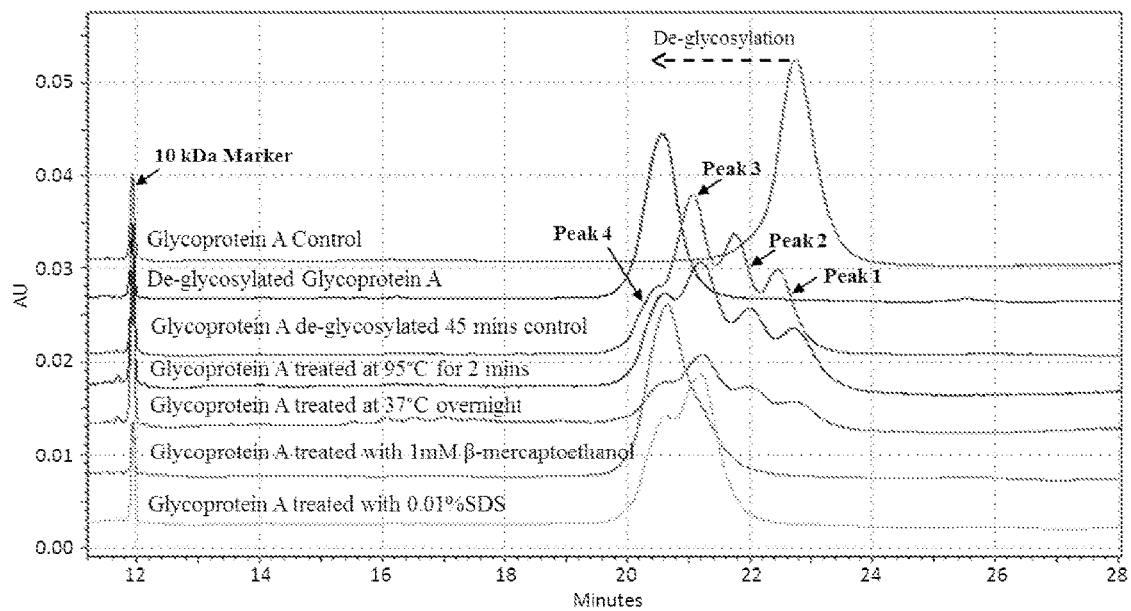
FIGURE 6 - Reduced CE-SDS profile of partially de-glycosylated glycoprotein A after partial denaturation

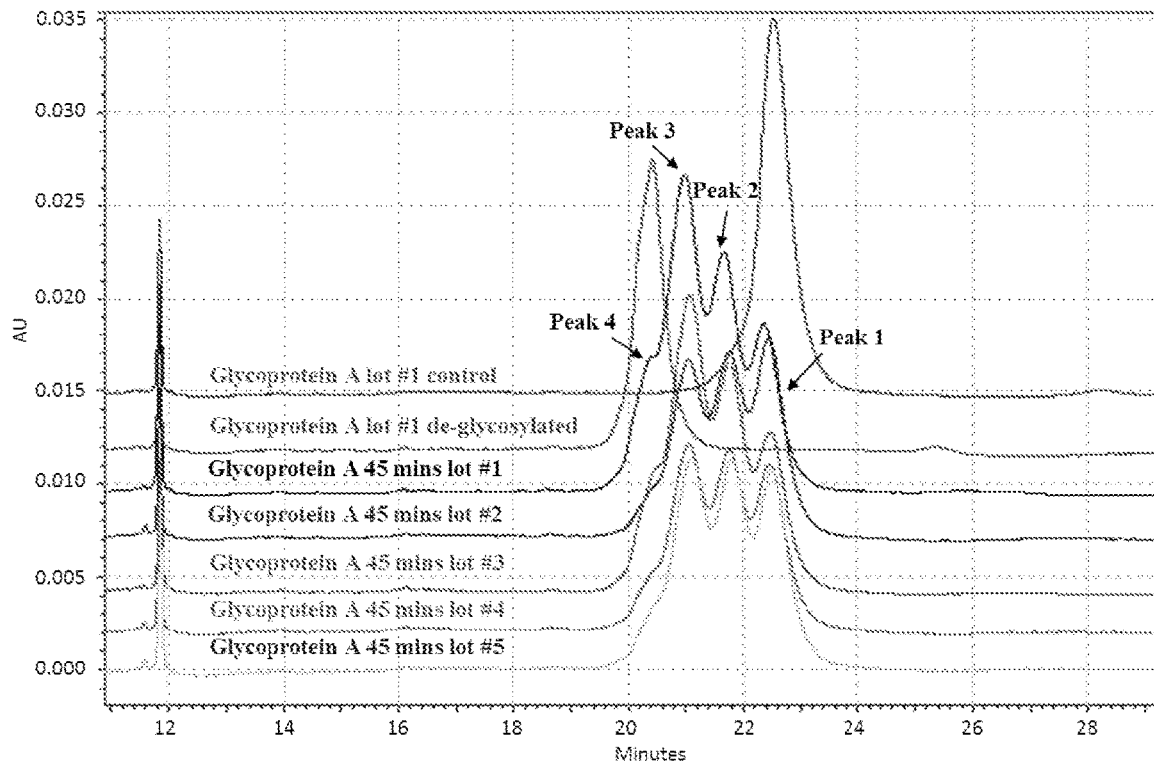
FIGURE 7 - Reduced CE-SDS profile of five lots of partially de-glycosylated glycoprotein A

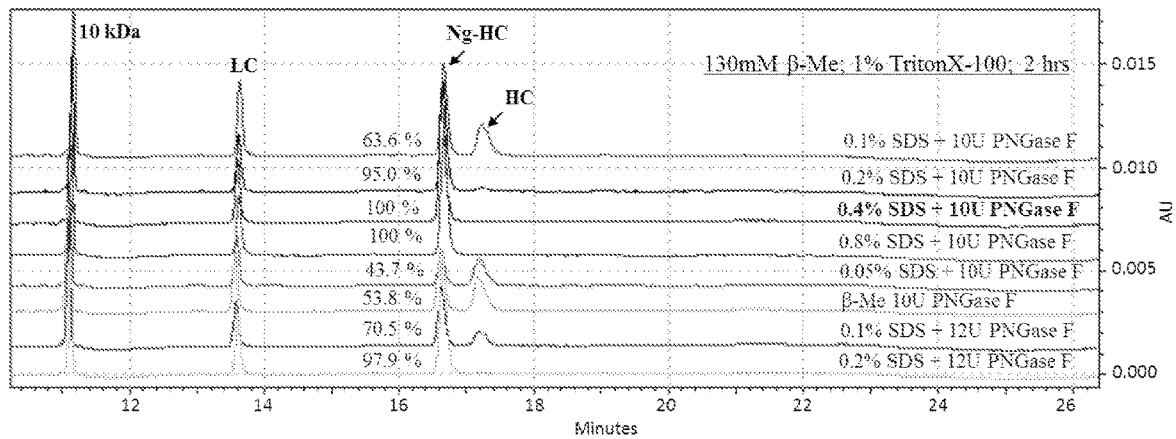
FIGURE 8 - Optimization SDS concentration for complete de-glycosylation of glycoprotein C under denaturing conditions
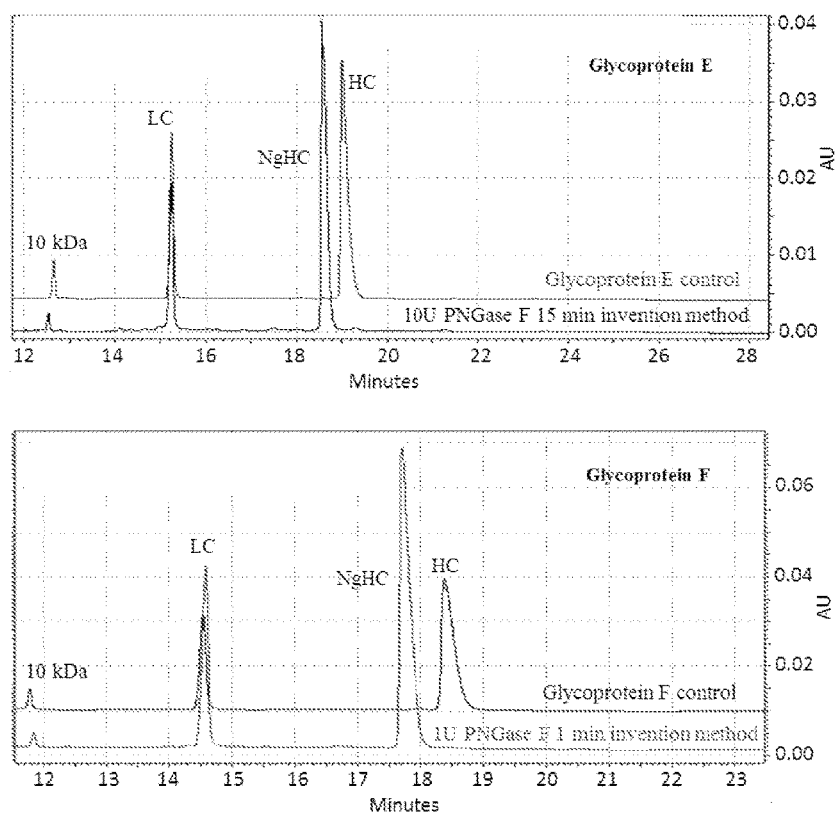
FIGURE 9 - Reduced CE-SDS profile of glycoprotein E and F de-glycosylated with invention method.

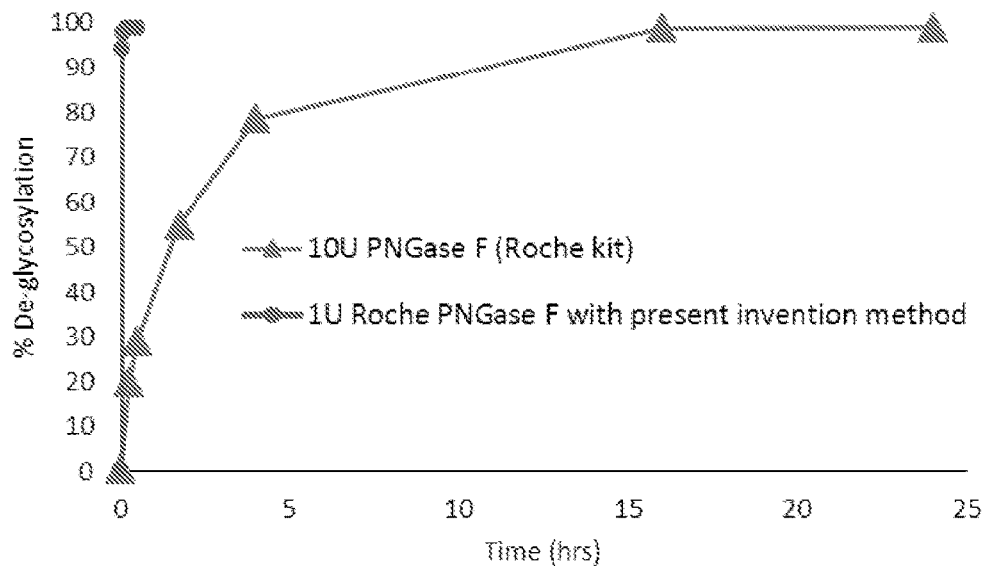
| Glycoprotein B (Fc glycosylated) |||| 
| 10U PNGase F (Roche kit) || 1U Roche PNGase F with our method (with denaturants) ||
| Time (hrs) | % De-glycosylation | Time (hrs) | % De-glycosylation |
| --- | --- | --- | --- |
| 0 | 0.4 | 0 | 0.4 |
| 0.25 | 19.7 | 0.017 (1 min) | 94.3 |
| 0.5 | 29.2 | 0.085 | 97.9 |
| 1.75 | 55 | 0.17 | 98.8 |
| 4 | 78.5 | 0.25 | 98.9 |
| 16 | 98.8 | 0.5 | 98.9 |
| 24 | 99 | -- | -- |
FIGURE 10 - De-glycosylation of Glycoprotein B: showing time course comparison of new method of present invention with Roche kit.

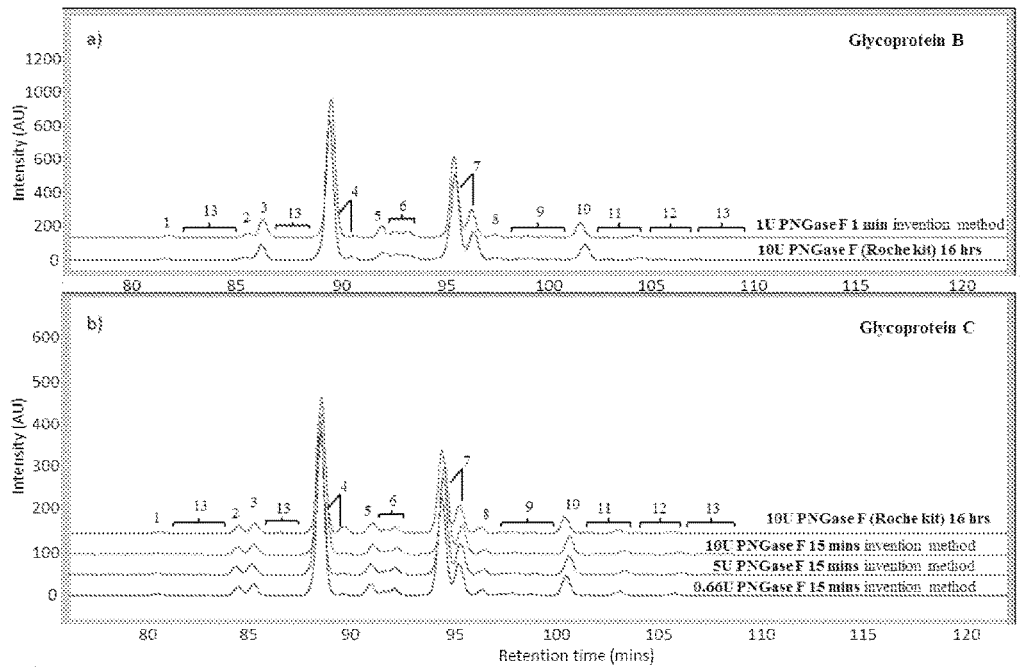
FIGURE 11 – Comparison of LC-glycan profile of glycoprotein B and C between invention method and Roche de-glycosylation kit.

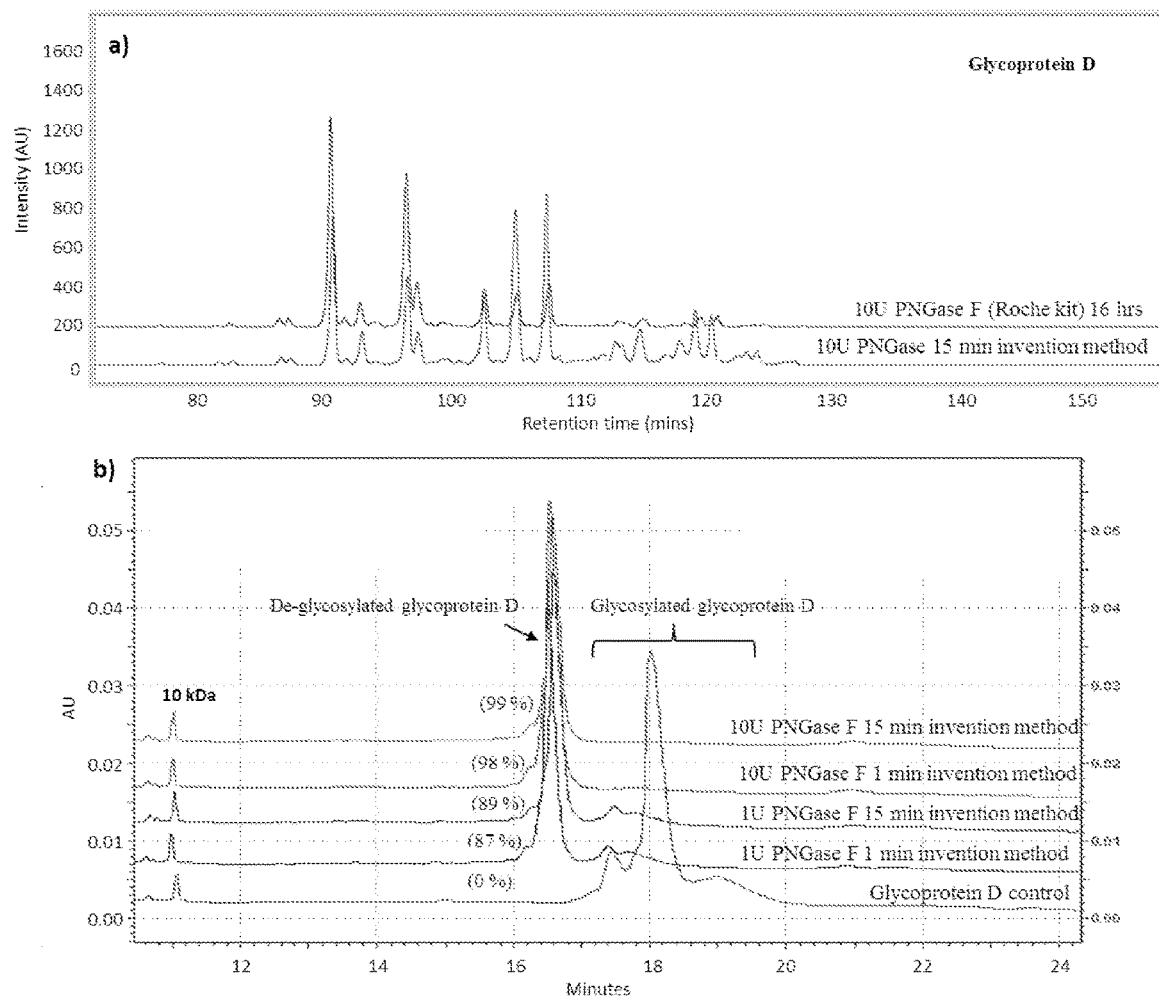
Figure 12 - Comparison of LC-glycan profile of glycoprotein D glycosylated at Fc, Fab and fusion part obtained from our method and Roche de-glycosylation kit.

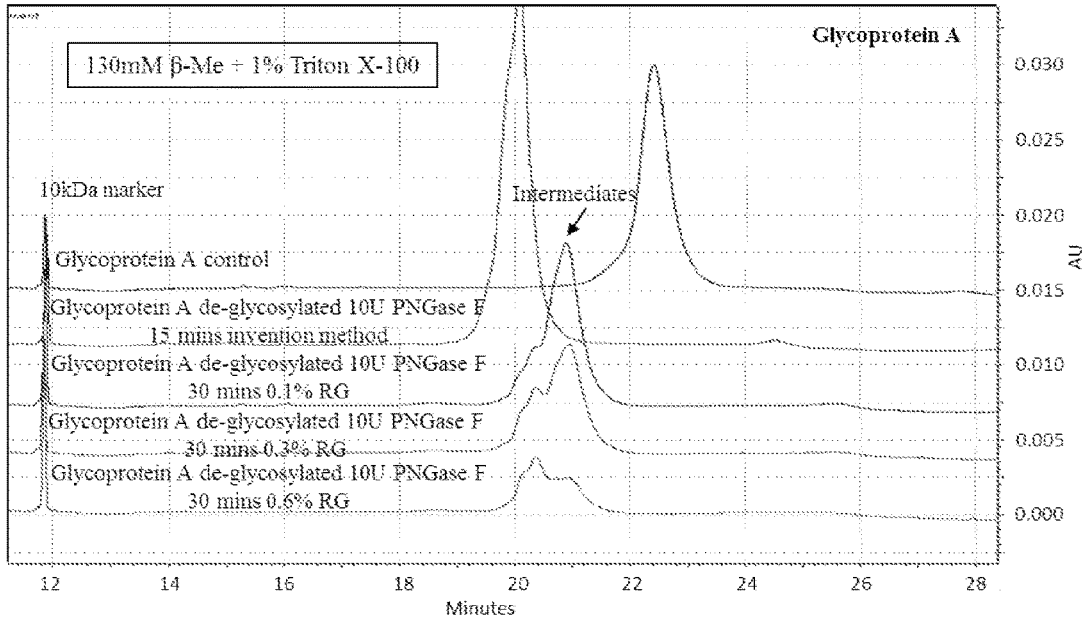
FIGURE 13 – Comparison of de-glycosylation of glycoprotein A using commercially available Waters' Rapigest (RG) with our recipe.
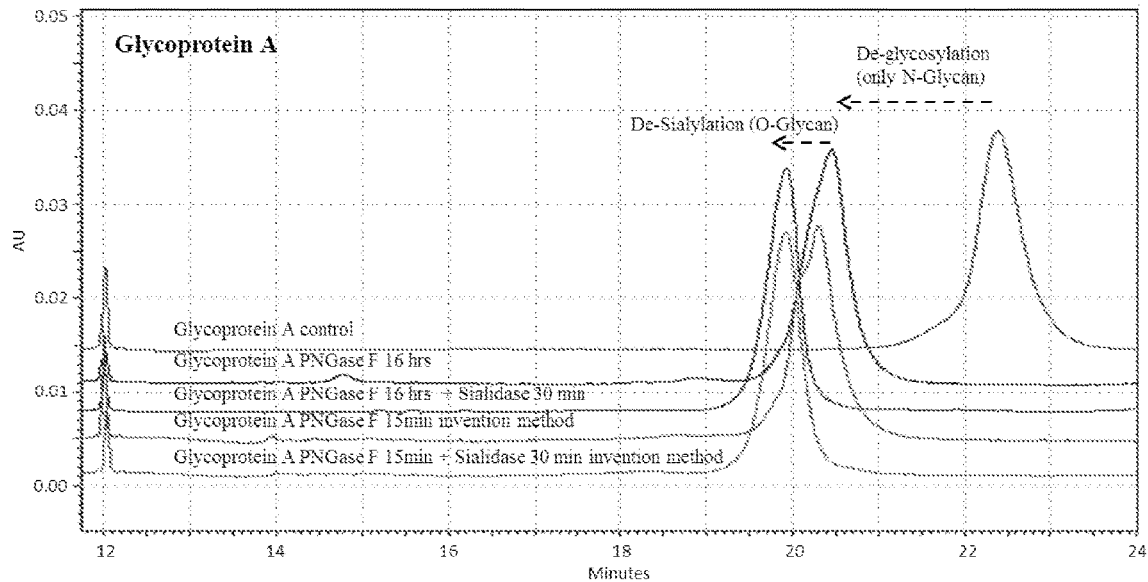
FIGURE 14 - Reduced CE-SDS profile of de-sialylated glycoprotein A using the present invention method.

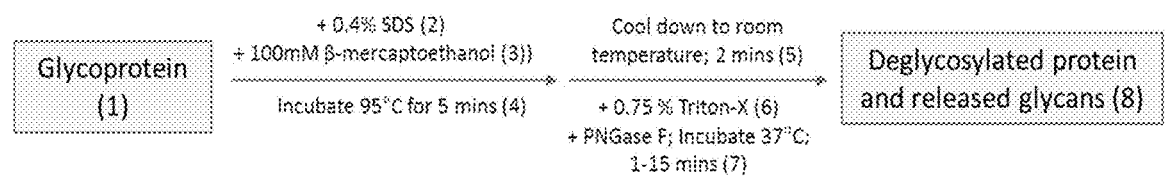
FIGURE 15- Steps involved in Protein De-glycosylation.

RAPID AND EFFICIENT DE-GLYCOSYLATION OF GLYCOPROTEINS

FIELD OF INVENTION

The present invention relates to rapid and reliable analytical methods, which are required by the industry to establish molecular similarity. It presents method for quick and efficient de-glycosylation of glycoproteins. It also relates to method of assessing molecular similarity by comparing tertiary structure of glycoproteins utilizing partial de-glycosylation as a tool.

BACKGROUND OF INVENTION

Glycosylation plays a critical role in protein folding, trafficking, and stability as well as cellular events such as receptor binding, cell signalling, immune recognition, inflammation and pathogenicity. Proteins of eukaryotic origin are often glycosylated as a result of post translational modification. Changes in specific glycan levels are often used as biomarkers in several diseases including diabetes, cancer, and infectious diseases. Since glycosylation is complex and heterogeneous, mapping the glycome can be an extremely challenging task and is generally done by liquid chromatography LC profiling of released glycan. Out of the two viz. N-linked and O-linked; the N-linked glycans are detached from glycoproteins by enzymatic cleavage with PNGaseF. Enzyme O-Glycosidase is commonly used for cleaving core 1 O-glycans, however pre-treatment with Neuraminidase enzyme is required to remove terminal sialic acids from O-Glycan. The secondary and tertiary structures of protein blocks access of the enzyme to the carbohydrates unless the protein is first denatured. Known protocols for denaturing involve the use of detergents or reducing agents, with an overnight incubation at 37° C.

The de-glycosylated protein can be useful for intact/reduced mass analysis in case of large and complex monoclonal antibodies which suffers due to inherent heterogeneity and insufficient ionization due to glycans. The released glycans can be labelled at their free-reducing terminus with a fluorescent dye for N-glycan profiling by methods such as high performance liquid chromatography (HPLC), capillary electrophoresis (CE), or mass spectrometry (MS).

The de-glycosylation of proteins by PNGaseF depend upon factors like: surface accessibility of glycans and steric hindrance by bulky and highly branched glycans. These factors are indirectly dependent on protein global conformation and glycan site occupancy, respectively. All these factors will determine the rate of de-glycosylation of a particular site on protein, which can be monitored by CE-SDS (capillary electrophoresis sodium dodecyl sulphate) utilizing difference in the molecular weight of de-glycosylated species. Thus, a partial de-glycosylation profile containing information on rate of de-glycosylation of different sites on the glycoprotein can serve as a fingerprint of its tertiary/quaternary conformation.

The glycans released after protein de-glycosylation is useful both for quality control and often for determining whether a protein will have a desired therapeutic efficacy or other effect. For a chromatographic mapping protocol, complete de-glycosylation of both proteins and peptides is often desirable. De-glycosylation may reduce smearing during protein separation by SDS-PAGE or may allow easier ionization and spectral interpretation during mass spectrometric analysis. This may be particularly useful when looking at intact molecular weights of proteins that may be skewed due to heterogeneity from abundance of post translation modifications. In the case of therapeutic antibodies, de-glycosylation is often necessary in characterizing modifications such as the presence of C-terminal lysine, or for labelled or drug-conjugated monoclonal antibodies, to monitor the number of small molecules coupled to the immunoglobulin.

In bio-pharma industries, criteria for approval include quality, efficacy and safety. Thus, assessing the molecular similarity of a candidate biosimilar to the innovator product is a critical task during development of a biosimilar product. For this purpose, rapid and reliable analytical methods are required by the industry to establish molecular similarity required by regulators.

Object of Invention

The object of present invention is to compare tertiary structure of glycoproteins utilizing partial de-glycosylation as a tool and to have a faster and efficient method for complete de-glycosylation of glycoproteins for analysis of glycans.

SUMMARY OF THE INVENTION

One object of the present invention is to provide a partial de-glycosylation method as a rapid tool to assess and compare tertiary/quaternary conformation of glycoprotein with multiple glycan sites. The method comprises addition of an endoglycosidase to native glycoprotein for limited period to partially cleave N-linked glycans in order to obtain sub-populations of partially de-glycosylated protein. The partially de-glycosylated glycoprotein is analysed using capillary electrophoresis.

Another object of the invention is to provide a method of complete de-glycosylation of a glycoprotein, wherein, glycoprotein is combined with anionic surfactant, reducing agent and non-ionic surfactant in order to obtain stable denatured glycoprotein. The denatured glycoprotein is further combined with non-ionic surfactant to counter the inhibitory effects of the anionic surfactant. An endoglycosidase is added to denatured glycoprotein to cleave N-linked glycans in order to obtain de-glycosylated protein. The released glycans are separated by liquid chromatography.

BRIEF DESCRIPTION OF DRAWINGS

FIG. 1 is reduced CE-SDS profile of partially de-glycosylated glycoprotein A. The glycoprotein which is fusion construct is de-glycosylated by 10 U PNGaseF at 37° C. with mixing at 300 rpm and aliquots were drawn out at multiple time intervals to be analyzed further by reduced CE-SDS analysis. The sub-populations of de-glycosylated glycoprotein are labelled as Peak 1, peak 2, peak 3 and peak 4. Completely de-glycosylated glycoprotein A was obtained by 16 hrs PNGaseF digestion.

FIG. 2 is reduced CE-SDS profile of glycoprotein C partially de-glycosylated by 10 U PNGaseF for 2 hrs at 37° C. under native conditions. The glycoprotein which is antibody has reduced to light chain (LC) and heavy chain (HC). Ng-HC corresponds to non-glycosylated heavy chain generated after partial PNGaseF digestion. Completely deglycosylated glycoprotein is obtained from 15 mins 10 U PNGaseF digestion at 37° C. in the presence of 0.4% SDS, 100 mM β-Me and 0.75% TRITON X-100™2-[4-(2,4,4-trimethylpentan-2-yl)phenoxy]ethanol.

FIG. 3 is reduced CE-SDS profile of partially de-glycosylated glycoprotein A by 10 U PNGaseF at 37° C. for under native conditions with or without mixing. A) Mixing at 300 rpm during PNGaseF incubation; B) No-mixing during PNGaseF incubation. Aliquots were drawn out at multiple time intervals to be analyzed further by reduced CE-SDS analysis. The sub-populations of de-glycosylated glycoprotein are labelled as peak 1, peak 2, peak 3 and peak 4.

FIG. 4 is reduced CE-SDS profile of glycoprotein A partially de-glycosylated under different buffer backgrounds by 10 U PNGaseF at 37° C. for 1 hr under native conditions. Buffer 1 is histidine formulation, buffer 2 is PBS trehalose formulation and buffer 3 is PBS formulation (PBS: Phosphate buffer saline).

FIG. 5 is reduced CE-SDS profile of partially de-glycosylated glycoprotein A by 10 U PNGaseF at 37° C. for 1 hr under native conditions demonstrating repeatability, inter day variability, inter-analyst variability of the method.

FIG. 6 is reduced CE-SDS profile of partially de-glycosylated glycoprotein A after partial denaturation. The samples were partially denatured by factors mentioned in the figure. The glycoprotein was de-glycosylated by 10 U PNGaseF at 37° C. with mixing at 300 rpm for 45 minutes. Completely de-glycosylated glycoprotein A was obtained by 16 hrs PNGaseF digestion.

FIG. 7 is reduced CE-SDS profile of five partially de-glycosylated batches of glycoprotein A. The glycoprotein was de-glycosylated by 10 U PNGaseF at 37° C. with mixing at 300 rpm for 45 minutes. Lot 1, 2 and 3 are licensed from EU and 4 and 5 from US. In the bottom panel the % distribution of sub-populations is tabulated.

FIG. 8 is optimization SDS concentration for complete de-glycosylation of glycoprotein which is an antibody under denaturing conditions. For fixing SDS concentration, the initial de-glycosylation experiments were carried out with 10 U PNGaseF, 130 mM β-Me, 1% TRITON X-100™2-[4-(2,4,4-trimethylpentan-2-yl)phenoxy]ethanol at 37° C. for 2 hrs.

FIG. 9 is reduced CE-SDS profile demonstrating complete de-glycosylation of glycoprotein E and F which are Fc glycosylated antibodies using method of present invention.

FIG. 10 is de-glycosylation time course comparison of new method of present invention with Roche de-glycosylation kit. The glycoprotein used is an antibody which is glycosylated at Fc region (glycoprotein B).

FIG. 11 is LC-glycan profile comparison between present invention method and Roche de-glycosylation kit. a) Fc glycan profile of antibody (glycoprotein B) obtained from 16 hrs Roche de-glycosylation method and from present invention method with 1 U PNGase F and 1 minute incubation time. b) Another Fc-glycan profile from glycoprotein C comparing glycan profiles obtained after de-glycosylation using decreasing units of PNGaseF (10 units to 0.66 units) in 15 minutes using present invention method. De-glycosylation using 16 hrs commercially available Roche de-glycosylation method was used as control. The relative abundance of the released glycans from glycoprotein B and C is tabulated comparing conventional 16 hrs digestion and present invention method. The peaks are numbered in the order of their elution where isomeric species are clubbed.

FIG. 12 is LC-glycan profile of glycoprotein D glycosylated at Fc, Fab and fusion part. The released glycans obtained using invention method and Roche de-glycosylation method are compared.

FIG. 13 is reduced CE-SDS profile demonstrating incomplete de-glycosylation of glycoprotein A using Waters' Rapigest (RG) detergent (0.1%-0.6%) as compared to complete de-glycosylation by present invention.

FIG. 14 is reduced CE-SDS profile of de-sialylation of glycoprotein A by Sialidase after PNGaseF digestion. Glycoprotein contains both N and O-glycans. N-glycans are removed by PNGase F before Sialidase treatment. Present invention method is used for de-glycosylation and compared with Sialidase used alone.

FIG. 15 shows a flow chart of the steps involved in protein de-glycosylation.

DETAILED DESCRIPTION

Definitions

The term "de-glycosylation" particularly refers to the process of removal of sugar entity (glycans) from a glycoprotein.

The term "partial de-glycosylation" particularly refers to intentional incomplete de-glycosylation resulting in mixture of glycosylated, de-glycosylated, glycoprotein and intermediates.

The term "complete de-glycosylation" particularly refers to complete removal of glycans from a glycoprotein wherein the entire volume is of de-glycosylated glycoproteins.

The term "glycoprotein" refers to an antibody, fragment thereof or fusion protein with multiple glycan sites.

The "commercially available kits" refer to SigmaP7367 kit, Prozyme GKE-5006 kit, Roche 11365177001 kit, NEB PNGaseF kit and Waters Rapigest kit.

Present invention describes a method with a rapid tool to assess and compare tertiary/quaternary conformation of glycoproteins with multiple glycan sites. This method utilizes the difference in exposure of glycan sites resulting in differential rates of de-glycosylation by PNGaseF. The sub-population of species created after partial de-glycosylation of multiple glycan sites at a particular time point is unique to a protein and is guided by factors such as surface accessibility of glycans, steric hindrance by bulky and highly branched glycans. This fingerprint is used to compare overall conformation of glycoproteins. Reduced CE-SDS was used to exploit the mass difference created because of partial de-glycosylation to segregate the populations.

The method of partial de-glycosylation of a glycoprotein for comparing tertiary structure method comprises steps of:
(a) providing a glycoprotein;
(b) combining the glycoprotein with endoglycosidase to partially cleave N-linked glycans in an amount from 1 unit to 10 units per 1 mg of glycoprotein;
(c) incubating components of step (b) at a temperature from about 37° C. for about 45 mins to 8 hrs to provide for a partially de-glycosylated protein.

Present invention further describes a rapid and efficient protein de-glycosylation method using detergents and reducing agents for the release of complex glycan structures to be further processed for LC profiling. The method was applied to large and complex glycoproteins wherein the attached oligosaccharides are often buried and are difficult to release. The novelty of the present method lies in unique combination of the components in right proportion that facilitates the enzymatic activity with minimum amount of enzyme used and in a very short time.

The method of de-glycosyation of a glycoprotein comprises the steps of:
(a) providing a glycoprotein;
(b) combining the glycoprotein with an anionic surfactant and reducing agent, wherein the reducing agent is in a sufficient amount to denature the glycoprotein;

(c) incubating components of step (b) at a temperature from 90° C. to 100° C. for 2 minutes to 5 minutes to provide for a denatured glycoprotein;
(d) cooling the denatured glycoprotein;
(e) combining the denatured glycoprotein with a non-ionic surfactant in an amount to counter the inhibitory effects of the anion surfactant
(f) introducing an endoglycosidase to cleave N-linked glycans in an amount from 0.66 unit to 10 units per 1 mg of denatured glycoprotein;
(g) incubating components of step (f) at 37° C. for 1 to 15 minutes to provide for a de-glycosylated protein; and
(h) separating the de-glycosylated protein from released glycans.

Methods and Materials

The glycoproteins including IgG1 mAbs and fusion proteins were produced in CHO cells and purified using standard antibody purification procedures at Biocon Ltd.

In one embodiment, glycoproteins are biosimilar of monoclonal antibodies and biosimilar of fusion proteins.

In another embodiment, the glycoproteins are monoclonal antibodies (mAbs) such as Itolizumab, Trastuzumab, bevacizumab, adalimumab etc.

In another embodiment, the glycoproteins are fusion proteins such as Etanercept etc.

The details of the glycoproteins are as mentioned below.
Glycoprotein A: Etanercept
Glycoprotein B: Itolizumab
Glycoprotein C: Trastuzumab
Glycoprotein D: Fusion mAb (Cetuximab+TGFRBII)
Glycoprotein E: Bevacizumab
Glycoprotein F: Adalimumab One part of the present invention is to provide a partial de-glycosylation method as a rapid tool to assess and compare tertiary/quaternary conformation of glycoprotein with multiple glycan sites. The method comprises addition of an endoglycosidase to native glycoprotein in 1 unit to 10 unit per 1 mg of glycoprotein for limited period such as for 45 mins to 8 hours to partially cleave N-linked glycans in order to obtain sub-populations of partially de-glycosylated protein. The partially de-glycosylated glycoprotein is analysed using capillary electrophoresis.

Second part of the present invention is to provide a method of complete de-glycosylation of a glycoprotein, wherein, glycoprotein is combined with anionic surfactant and reducing agent and incubated at 90-100° C. for 2 mins to 5 mins. Further non-ionic surfactant is added in order to obtain stable denatured glycoprotein. The denatured glycoprotein is further combined with non-ionic surfactant to counter the inhibitory effects of the anionic surfactant. An endoglycosidase is added 1-10 unit per 1 mg of denatured glycoprotein and incubated for 1-15 mins of time at 37° C. to cleave N-linked glycans in order to obtain de-glycosylated protein. An exoglycosidase 0.1 unit per 1 mg added to denatured glycoprotein after non-ionic surfactant or de-glycosylated protein after endoglycosidase and incubated for 30 mins at 37° C. to cleave terminal sialic acid of N- and O-glycans to obtain a de-sialylated protein of denatured glycoprotein. The released glycan are separated by liquid chromatography.

An exoglycosidase is optionally added to denatured glycoprotein after non-ionic surfactant or de-glycosylated protein after endoglycosidase to cleave terminal sialic acid of N- and O-glycans to obtain a de-sialylated protein of denatured glycoprotein.

In one embodiment, the anionic surfactant is a member selected from the group consisting of SDS (Sodium dodecyl sulfate), carboxylates, sulphonates, petroleum sulphonates, alkylbenzenesulphonates, naphthalenesulphonates, olefin sulphonates, alkyl sulphates, sulphates, sulphated, natural oils & fats, sulphated esters, sulphated alkanolamides and alkylphenols.

In preferred embodiment, the anionic surfactant used for denaturation of glycoprotein is SDS.

The reducing agent is in an amount to break disulphide bonds and is selected from the group consisting of β-mercaptoethanol, dithiothreitol, or tris (2-carboxyethyl) phosphine In preferred embodiment, the reducing agent is β-mercaptoethanol in an amount of 100 mM to 150 mM.

The non-ionic surfactant is a member selected from the group consisting of TRITON X-100™2-[4-(2,4,4-trimethylpentan-2-yl)phenoxy]ethanol, ethoxylated aliphatic alcohols, polyoxyethylene surfactants, carboxylic esters, polyethylene glycol esters, anhydrosorbitol ester & it's ethoxylated derivatives, glycol esters of fatty acids, carboxylic amides, monoalkanolamine condensates and polyoxyethylene fatty acid amides In one embodiment, the non-ionic surfactant such as TRITON X-100™2-[4-(2,4,4-trimethylpentan-2-yl)phenoxy]ethanol is added to counter effect inhibitory effects of SDS.

In preferred embodiment, TRITON X-100™2-[4-(2,4,4-trimethylpentan-2-yl)phenoxy]ethanol is added at a concentration of 0.60% to 1.2%.

In another embodiment, commercially available SF surfactant such as Waters Rapigest kit for denaturation of protein followed by de-glycosylation using Roche PNGase F was also used to compare performance of present invention.

In one part, the endoglycosidase such as PNGaseF was added to denatured glycoprotein to cleave N-linked glycans from glycoproteins where the innermost GlcNAc residue may or may not be linked to α1-6 fucose residue to obtain complete de-glycosylated glycoprotein. The time required is between 1 to 15 minutes.

In another part, endoglycosidase is PNGaseF, which was added to native glycoprotein for 45 mins to 8 hrs to partially cleave N-linked glycans from glycoproteins where the innermost glycan residue is GlcNAc to obtain partial de-glycosylated glycoprotein.

The exoglycosidase such as Sialidase was added to denatured and N-Glycan de-glycosylated glycoprotein to cleave terminal sialic acid from O-linked glycans from glycoproteins In preferred embodiment, the Sialidase enzymatic reaction carried out at 37° C. for 30 mins to obtain de-sialylated protein.

De-glycosylation under native conditions was performed as follows.

The PNGaseF (Roche, cat. 11365193001) was used to remove the N-glycan by incubating 1 mg of each glycoprotein in 50 mM Tris Cl pH 8.0, 1 mM CaCl2 with 10 units of PNGaseF at 37° C. for 16 hours for complete de-glycosylation. For partial de-glycosylation incubation was for shorter time as indicated on respective figures.

For Sialidase digestion (QABio, E-S001), 0.1 Units of Sialidase was added to 1 mg of each glycoprotein in 50 mM Sodium acetate pH 4.5 and incubated for 30 mins at 37° C. The samples were frozen at −20 C till the analysis was performed.

De-glycosylation under denaturing conditions was performed as follows.

1 mg of each glycoprotein in 50 mM Tris Cl pH 8.0, 1 mM CaCl2 was mixed with 100-130 mM β-mercaptoethanol and 0.1-0.8% of SDS from 10% stock solution. The mix was incubated at 95° C. for 2 minutes and the cooled down to room temperature (2 minutes). 0.75-1% TRITON X-100™2-[4-(2,4,4-trimethylpentan-2-yl)phenoxy]ethanol was added and vortexed followed by 1-10 units of PNGaseF enzyme (Roche, cat. 11365193001) and incubated at 37° C. for 1-15 minutes.

For Sialidase digestion, 0.1 Units of Sialidase was added to 1 mg of each glycoprotein in 50 mM Sodium acetate pH 4.5 and incubated for 30 mins at 37° C. The glycoprotein for Sialidase digestion was pre-treated with 10 units of PNGase F in the presence of 0.4% SDS, 100 mM β-mercaptoethanol and 0.75% TRITON X-100™2-[4-(2,4,4-trimethylpentan-2-yl)phenoxy]ethanol as mentioned above. The samples were frozen at −20° C. till the analysis was performed.

Sample preparation for NP HPLC-FLD of glycans was performed as follows

The released glycans were separated from the protein by adding chilled ethanol followed by centrifugation for 15 min at 8000 rpm. The supernatant containing the glycans was collected and vacuum dried. Labelling reagent was prepared by dissolving 5 mg of Anthranillic acid and 6 mg of Sodium cyano borohydride in 100 µL of a 70:30 DMSO: Glacial acetic acid mixture. Five µL of this reagent was added to the dried glycan sample and incubated at 80° C. for 45 min. The labelled glycans were then reconstituted in water and washed with ethyl acetate 5 times. The excess ethyl acetate is removed each time using phase separation of organic and aqueous layers and the samples are again vacuum dried. The dried samples are reconstituted in 100 µl of 50% acetonitrile and 50% water (v/v) and mixed thoroughly. The supernatant is removed and transferred to a maximum recovery vial and injected in to HPLC system with a fluorescent detector. The glycans were separated on LudgerSep N2 Amide Column with mobile phase A as 100% Acetonitrile and B as 50 mM Ammonium Formate pH 4.4. The fluorescent detector was set at excitation 352 nm and emission 435 nm. The glycan samples can be stored at 2-8° C. till the analysis.

CE-SDS sample preparation and instrument operating procedure as follows

The CE-SDS analysis was performed on PA 800 Plus Pharmaceutical Analysis System (Beckman Coulter) with 32 karat V 9.1 software. Capillary of 30 cm length was used with 50µ ID and aperture of 200µ. Samples were prepared by desalting 125 µg of glycoprotein using SDS buffer pH 9.5 in a 10 kDa MWCO NanoSep. 76 µl SDS buffer of pH 9.5 was mixed with 19 µl of desalted sample along with 0.5 µl internal standard (10 kDa mol. wt. marker, SDSMW analysis kit) and 5 µl β-mercaptoethanol. The mixture is vortexed and briefly centrifuged. The contents were incubated at 80° C. for 2 minutes and cooled down the solution to room temperature. The contents were transferred to PCR tube placed in a universal vial.

The de-glycosylation methods were carried out as per method of present invention (FIG. 1-9) and then compared with pre-existing commercially available de-glycosylation methods by Roche and Waters Rapigest (FIG. 10-13). The use of method is also extended to Sialidase enzymatic digestion of glycoproteins with O-linked glycans (FIG. 14).

Example 1

A time course for de-glycosylation of a multiple glycan site glycoprotein A by PNGaseF under native conditions is illustrated in FIG. 1, which is Reduced CE-SDS profile of partially de-glycosylated glycoprotein A which is a fusion construct of antibody. The reduced CE-SDS profile showed that at different time intervals different sub-populations of glycoprotein are obtained where each consecutive peak correlates directly to de-glycosylation of a distinct glycan site in the protein.

In FIG. 1 glycoprotein A showed 3 distinct glycan sites (6 in dimeric form), the partial de-glycosylation of which lead to 4 distinct peaks. Peak 1 was completely glycosylated, followed by peak 2 and 3 with one and two sites de-glycosylated respectively. Further peak 4 had all three glycan sites de-glycosylated and was completely de-glycosylated glycoprotein A. As the incubation time for de-glycosylation progressed, the glycan site sub-populations shifted toward complete de-glycosylation (left side). The intensities of each sub-population at each time interval reflected accessibility of glycan sites which can be masked by protein local conformation and steric hindrance by bulky and highly branched glycans (site occupancy). This profile therefore is a fingerprint of glycosylated protein tertiary structure and can be used as a tool for assessing higher order structure quality. The profiles are much simpler in single glycan site glycoprotein (2 in dimeric form) as seen in FIG. 2, which is reduced CE-SDS profile of glycoprotein C partially de-glycosylated by 10 U PNGase F at 37° C. under native conditions. The glycoprotein C which is an antibody has reduced to light chain (LC) and heavy chain (HC). Ng-HC corresponds to non-glycosylated heavy chain generated after partial PNGaseF digestion. The size variants due to heterogeneity in glycan structures at a particular site are assumed to be covered in peak width of each sub-population (because of low molecular weight difference). The sub-populations at a particular time point are sensitive to multiple factors like temperature, length of incubation, enzyme units and mixing at the time of incubation. Both reducing temperature and reducing enzyme units will reduce the rate of enzymatic reaction resulting in less de-glycosylated sub-populations. The effect of length of incubation and mixing is demonstrated in FIG. 1 and FIG. 3, respectively.

The interference from buffer matrix on PNGase F digestion was also evaluated and the assay was insensitive to protein buffer (FIG. 4). Thus the parameters should be optimized to get the best profile containing well resolved glycan sub-populations of the glycoprotein. For our experiments, we chose the glycoprotein profile at 45 minutes incubation time with mixing at 300 rpm, 10 U of PNGaseF enzyme at 37° C.

The analytical method variability was established at 45 minutes de-glycosylation of glycoprotein A under native conditions and evaluated based on intra-day reproducibility/repeatability, inter-day and inter-analyst runs. In Table 1, the relative abundance of each sub-population shown in FIG. 1 is tabulated and % RSD calculated. Maximum variability was observed for the species lower in abundance and not well-resolved sub-populations. The reduced CE-SDS profiles of glycoprotein A demonstrating method variability are overlaid in FIG. 5.

TABLE 1

Analytical method variability evaluated
for intra-day, inter-day and inter-analyst.
Each sub-population is estimated as relative area
percentage of peak 1, 2, 3 and 4.

| Parameters evaluated | Sub-Populations | | | |
|---|---|---|---|---|
| | Peak 4 | Peak 3 | Peak 2 | Peak 1 |
| Day 1 | 24.0 | 46.6 | 19.9 | 9.6 |
| | 27.1 | 45.6 | 18.9 | 8.5 |
| | 25.9 | 47.5 | 18.0 | 8.6 |
| Intra-day % RSD | 6.0 | 2.1 | 5.0 | 6.7 |
| Day 2 | 23.4 | 49.7 | 18.4 | 8.5 |
| | 23.7 | 49.3 | 19.1 | 8.0 |
| | 21.0 | 48.3 | 20.6 | 10.1 |
| Inter-day % RSD | 8.7 | 3.3 | 5.0 | 9.0 |
| Day 2 | 22.9 | 49.0 | 19.0 | 9.1 |
| | 23.6 | 49.5 | 19.1 | 7.9 |
| | 20.9 | 47.9 | 20.7 | 10.6 |
| Inter-analyst % RSD | 5.6 | 1.5 | 4.7 | 12.3 |

We estimated the effect of partial denaturation/unfolding of antibody by multiple factors on the sub-populations of partially de-glycosylated antibody to evaluate the robustness of the method. The denatured samples were obtained by exposure to heat, detergents and reducing agents prior to PNGaseF digestion. Both heat and detergent affected the hydrogen bonding and hydrophobic interactions. Reducing agents target the di-sulphide linkages in proteins. Reduced CE-SDS profile of partially de-glycosylated glycoprotein A by 10 U PNGase F at 37° C. with mixing at 300 rpm for 45 minutes after partial denaturation. Completely de-glycosylated glycoprotein A was obtained by 16 hrs PNGase F digestion. As seen in FIG. 6, each of the above-mentioned factors influenced the sub-populations of de-glycosylation conformers to different extent. For instance, maximum shift to peak 3 and 4 (towards complete de-glycosylation) is seen in protein treated with 0.01% SDS or 2-mercaptpethanol. Both overnight incubation of the antibody at 37° C. and 2 min incubation at 95° C. resulted in significant shifts in sub-populations compared to regular 45 minutes partially de-glycosylated glycoprotein used as a control. The results obtained upon overnight incubation at 37° C. had its implication over stability comparisons of de-glycosylated glycoprotein with glycosylated antibody. In most cases, the differences observed would be a combinatorial effect of mild protein denaturation due to enzymatic treatment for extended incubations and the structural distortions after glycan removal rather than the latter alone. The shifts in protein glycan sub-populations indicates that the changes in protein tertiary structure imposed by partial denaturation directly affects the amount of de-glycosylation at related site in the glycoprotein and the levels of sub-populations can therefore be used to compare protein quaternary/tertiary structures.

In order to use the method for comparing higher order structures it was tested on multiple lots of glycoprotein A approved from EU and US regulatory agencies. Reduced CE-SDS profile in FIG. 7 of five partially de-glycosylated lots of glycoprotein A were obtained. The glycoprotein was de-glycosylated by 10 U PNGaseF at 37° C. with mixing at 300 rpm for 45 minutes. Lot 1, 2 and 3 are licensed from EU and 4 and 5 from US. FIG. 7 shows the reduced CE-SDS traces of 3 EU and 2 US lots of glycoprotein A. As evident, significant variability was observed among the batches analysed which is more than the method variability. Glycoprotein A is complexly glycosylated at both Fc and fusion domain, the difference observed can come if the glycan site occupancy in the lots is not similar. The differential distribution of bulky and branched glycans in multiple lots of glycoprotein A will cause different levels of steric hindrance to the PNGaseF digestion causing altered CE-SDS profiles. However, the N-glycan profiles of both EU and US lots are similar. In Table 2 one representative EU and US lots are compared for their LC glycan profile and are found to be similar. These lots showed very different partial de-glycosylated reduced CE profile (FIG. 7). This suggested that the lot-to-lot variability observed for antibody A is coming from protein conformation at the site of glycan attachment. Nevertheless, both site occupancy and protein conformation at the site of glycan attachment can influence sub-populations in partially de-glycosylated sample. Since glycans are known to affect biological activity of monoclonal antibodies, in antibody manufacturing, the variability in glycan profiles of different lots is minimized in order to maintain the efficacy of the product and therefore the lot-to-lot differences observed above are real. Thus, the method is sensitive and suitable for mapping lot-to-lot variability in tertiary structure of innovator product and comparing with biosimilar.

TABLE 2

LC glycan profile comparison of of lots of glycoprotein A showing maximum difference in reduced CE-SDS profile. The numbers correspond to relative abundance of glycan species in the lots.

| Glycoprotein A | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Lot #4 | 0.2 | 0.3 | 0.9 | 16.1 | 3.4 | 1.1 | 13.1 | 1.5 | 5 | 5 | 14 | 24.7 | 10.7 | 1.3 | 0.4 | 2.4 |
| Lot #1 | 0.2 | 0.4 | 0.9 | 16.3 | 2.7 | 1.4 | 13.2 | 1.4 | 5.6 | 6.5 | 14 | 24.4 | 9.6 | 0.9 | 0.3 | 2.2 |

The glycans released after protein de-glycosylation is useful both for quality control and for determining whether a protein will have a desired therapeutic efficacy or other effect. For a chromatographic mapping protocol, and for other analytical scenarios, complete de-glycosylation of both proteins and peptides is often desirable. For example, de-glycosylation may reduce smearing during protein separation by SDS-PAGE or may allow easier ionization and spectral interpretation during mass spectrometric analysis. This may be particularly useful when looking at intact molecular weights of proteins that may be skewed due to heterogeneity from an abundance of PTM's. In the case of therapeutic antibodies, de-glycosylation is often necessary in characterizing modifications such as the presence of C-terminal lysine, or for labelled or drug-conjugated monoclonal antibodies, to monitor the number of small molecules coupled to the immunoglobulin. For this reasons, it is often advantageous to de-glycosylate glycoproteins.

In present invention, we show a rapid and efficient protein-de-glycosylation method using detergents and reducing agents. The flowchart of the steps followed for protein de-glycosylation is depicted in FIG. 15. The description of each step is elaborated in Table 3.

TABLE 3

Description of the method. The step number correspond with the flowchart.

| Step No. | Description | Procedure | Significance |
| --- | --- | --- | --- |
| 1 | Glycoprotein | 1 mg of protein is taken in 2 mg/ml concentration in micro-centrifuge tube. Dilution in Tris buffer pH 8. | Endo-glycosidase activity is optimum in Tris buffer pH 8. |
| 2 | Sodium dodecyl sulphate | SDS is added to the final concentration of 0.4% and the tube is inverted 3 times quickly to avoid precipitation of proteins. | SDS is a denaturant that unfolds the protein and expose the glycans for efficient enzymatic activity. |
| 3 | β-mercaptoethanol | β-Me is added to the final concentration of 100 mM and vortexed. | β-Me reduces disulphide linkages and help in protein unfolding. |
| 4 | Incubation | Incubate the reaction mixture at 95° C. for 2-5 minutes. | High temperature helps in unfolding. |
| 5 | Cool down | Cool down to room temperature for 2 minutes | Required for enzyme addition. |
| 6 | Triton-X 100 | Add triton X-100 to the final concentration of 0.75% of and vortexed. | Trion X-100 is a non-ionic detergent and counteracts SDS for its inhibitory effect on enzyme activity. |
| 7 | PNGaseF | Add 1 U of Roche PNGaseF and incubate at 37° C. for 1-15 minutes. | PNGaseF is an enzyme that cleaves N-glycan from proteins. |
| 8 | De-glycosylated protein and released glycans | | The released glycans are processed further for N-glycan profiling. The de-glycosylated protein can be further processed for MS analysis. |

Example 2

Briefly, anionic detergent SDS (0.4%) and reducing agent β-mercaptoethanol (100 mM) were used for unfolding the protein at 95° C. The protein was then treated with non-ionic detergent TRITON X-100™2-[4-(2,4,4-trimethylpentan-2-yl)phenoxy]ethanol (0.75%) prior to de-glycosylation by PNGaseF to counter the inhibitory effects of SDS. One mM calcium chloride was used in reaction buffer (10 mM Tris-Cl pH 8.0) to stabilize and promote PNGaseF activity. The reaction optimization conditions are detailed in FIG. 8 wherein optimization SDS concentration for complete de-glycosylation of antibody C under denaturing conditions is illustrated. For fixing SDS concentration, the initial de-glycosylation experiments were carried out with 10 U PNGaseF, 130 mM β-Me, 1% TRITON X-100™2-[4-(2,4,4-trimethylpentan-2-yl)phenoxy]ethanol at 37° C. Complete de-glycosylation with 10 U of enzyme in 15 mins was also observed for other Fc glycosylated antibodies (glycoprotein E and F) with present invention method (FIG. 9).

The novelty of the present method lies in unique combination of the components in right proportion that facilitates the enzymatic activity with minimum amount of enzyme used to complete the process in a very short time that is between 1 to 15 minutes. As shown in Table 4, in commercially available kits 10-25 units of enzyme have been shown to release N-glycans from 1 mg of denatured protein (see specific activity). In present method, with in-house developed protocol as per Table 3, 1 unit of enzyme (Roche enzyme tested) was able to digest ~95% of 1 mg of denatured protein in 1 minute which was almost tenfold increase in enzymatic activity and significant reduction in time compared to 1 hr to overnight incubation in commercially available kits (Table 4).

TABLE 4

De-glycosylation kits available in market. All the ingredients used in the de-glycosylation mix are easily available and commonly used for protein denaturation.

| Product (PNGaseF) | Reaction condition | Unit definition | IUB unit | Specific activity |
| --- | --- | --- | --- | --- |
| Sigma P7367 | SDS: 0.2% βMe: 100 mM Triton-X: 1.2% Reaction time: 1-3 hrs | One unit will catalyze the release of N-linked oligosaccharides from 1 nanomole of denatured Ribonuclease B in 1 minute at 37° C. at pH 7.5 | 1 Sigma unit = 1 IUB miliunit | 10 U/mg ≥25 U/mg |
| Prozyme GKE-5006 | SDS: 0.1% βMe: 50 mM NP-40: 0.75% Reaction time: 2 hours-overnight | One unit of N-Glycanase is defined as the amount of enzyme required to catalyze the release of N-linked oligosaccharides from 1 μmole of denatured Ribonuclease B per minute at pH 7.5 and 37° C. | 1 Prozyme unit = 1 IUB unit | 25 U/mg |
| Roche kit 11365177001 | Reaction time: Overnight without the detergents. Denaturation by SDS increases the glycosylation rate considerably (1-2 hours) SDS: up to 0.2% βMe: 1% Triton-X/NP-40: 0.5-2% | One unit will catalyze the release of N-linked oligosaccharides from 1 nanomole of denatured dabsyl fibrin glycopeptide in 1 minute at 37° C. at pH 7.8 | 1 Roche unit = 1 IUB miliunit | 10 U/mg |
| NEB PNGaseF | SDS: up to 0.5% DTT: 40 mM NP-40: 1% Reaction time: 1 hr. | One unit is defined as the amount of enzyme required to remove >95% of the carbohydrate from 10 μg of denatured RNase B in 1 hour at 37° C. in a total reaction volume of 10 μl 10.8 ug/milli-unit | 65 NEB units = 1 IUB milliunit | 1800000 U/mg |

Example 3

FIG. 10 compares the time course of percentage de-glycosylation of Fc glycosylated antibody glycoprotein B with Roche kit (10 U of Roche enzyme—without denaturants) and with Biocon's method (1 U of Roche enzyme with denaturants). As observed nearly complete de-glycosylation (~99%) was observed with 10 U of Roche enzyme without denaturation in 16 hrs whereas the similar glycan yield (~94%) was achieved in 1 min with 1 U of Roche enzyme used in method of present invention.

Example 4

FIG. 11 gives a comparison of LC profile of glycan species from two Fc glycosylated monoclonal antibodies (glycoprotein B and C) obtained with less enzyme units and reduced incubation time using method of present invention and Roche kit. Identical profiles are obtained for glycoprotein B digested with 10 U enzyme for 16 hr and 1 unit of enzyme for 1 min. Similar glycan yield was obtained for glycoprotein C digested with 0.66 U enzyme for 15 min as compared to 10 U enzyme for 16 hr. Minor glycan species (<0.5%) were observed with 10 U Roche enzyme alone for 16 hrs. Similar glycan species were observed in present invention method upon 1-minute 1 unit enzyme incubation (FIG. 11).

The glycoproteins tested in present invention are monoclonal antibodies/fusion antibodies (>100 kDa) which are structurally complex and heavily glycosylated at their Fc, Fab and fusion parts. FIG. 12 panel shows LC-glycan profile of heavily glycosylated fusion glycoprotein D with Fc, Fab and fusion part glycosylated at 6 distinct sites (12 in dimer). Additional glycan species were released with present method which otherwise were not accessible to PNGaseF for digestion. These glycan species correspond to highly branched and bulky galactosylated and sialylated species present in the Fab and fusion part of the protein. In panel b CE profile of de-glycosylated fusion protein (glycoprotein D) is depicted wherein 87% of de-glycosylation is observed using 1 unit enzyme incubated for 1 minute with invention method and the digestion was complete with 10 units of enzyme in 1 minute. The relative percentage of de-glycosylation is mentioned in panel b of the FIG. 12.

Furthermore, as shown in FIG. 13, the invention method was also efficient in completely de-glycosylating multiple glycan site fusion protein (Glycoprotein A) in similar time and enzyme quantity.

Example 5

We extended similar recipe of detergents and reducing agents for de-glycosylation by enzymes other than PNGaseF. In FIG. 14, comparison of Sialidase digestion with and without detergents is shown. The Sialidase in our recipe is capable of de-sialyting O-glycans (removal of terminal sialic acid) similar to Sialidase alone i.e. in 30 mins. The protein used is N-glycan de-glycosylated using PNGase F prior to Sialidase treatment. The method can be further optimised to reduce the incubation time as well as enzyme units.

The method can be analysed further by adding other endoglycosidase enzymes such as Beta-galactosidase, N-acetylglucosaminidase, endo-H, endo-F2, endo-S, mannosidase and fucosidase to remove respective terminal sugar residues.

Example 6

We also compared the performance of commercially available Waters Rapigest kit for denaturation and then subsequent de-glycosylation by Roche PNGase F. FIG. 13 illustrates reduced CE-SDS profile demonstrating de-glycosylation of glycoprotein A using present invention method and commercially available Waters Rapigest (RG) kit. The results show that present invention method for de-glycosylation is better than commercially available/traditional methods since it has benefits of reduced time, reduced cost and reduced enzyme units. The present invention not only permits faster de-glycosylation of glycoproteins, but also improve both the yield and number of glycan species released.

The rapid de-glycosylation method has following merits and application.

1) De-glycosylation of structurally complex glycoproteins, which are heavily glycosylated.
2) Complete N-Glycan LC-MS profiling including exoglycosidase array of intact glycoproteins including N and O-glycans.
3) Intact and reduced mass analysis of glycoproteins which suffers due to inherent inhomogeneity and low ionization of exposed glycans. The detergents can be removed prior to MS analysis using desalting spin columns. Multiple post digestion clean-up protocols are also available in literature which removes detergents from the reaction mixture.
4) Identification of glycosylation sites and site occupancy using MS which is difficult otherwise because of glycan heterogeneity at the site of attachment.

The invention claimed is:

1. A method of complete N-glycan de-glycosylation of a glycoprotein, wherein, the method comprising steps of:
   (a) providing a glycoprotein;
   (b) combining the glycoprotein with an anionic surfactant and reducing agent, wherein the reducing agent is in a sufficient amount to denature the glycoprotein and the anionic surfactant is in a concentration of 0.1% to 0.8%;
   (c) incubating components of step (b) at a temperature from 90° C. to 100° C. for 2 minutes to 5 minutes to provide for a denatured glycoprotein;
   (d) cooling the denatured glycoprotein;
   (e) combining the denatured glycoprotein with a non-ionic surfactant in an amount to counter the inhibitory effects of the anionic surfactant, where the non-ionic surfactant is in a concentration of 0.6% to 1.2%;
   (f) introducing an endoglyrosidase to cleave N-linked glycans in an amount from 0.66 unit to 10 units per 1 mg of denatured glycoprotein;
   (g) incubating components of step (f) at 37° C. for 1 to 15 minutes at atmospheric pressure to provide for a completely de-glycosylated protein; and
   (h) separating the completely N-glycan de-glycosylated protein from released glycans.

2. The method of claim 1, wherein the anionic surfactant is selected from the group consisting of SDS (sodium dodecyl sulfate), carboxylates, sulphonates, petroleum sulphonates, alkylbenzenesulphonates, naphthalenesulphonates, olefin sulphonates, alkyl sulphates, sulphates, sulphated natural oils and fats, sulphated esters, sulphated alkanolamides and alkylphenols.

3. The method of claim 2 wherein said anionic surfactant is sodium dodecyl sulfate (SDS).

4. The method of claim 1, wherein the non-ionic surfactant is selected from the group consisting of 2-[4-(2,4,4- trimethylpentan-2-yl)phenoxy]ethanol, ethoxylated aliphatic alcohols, polyoxyethylene surfactants, carboxylic esters, polyethylene glycol esters, anhydrosorbitol ester and its ethoxylated derivatives, glycol esters of fatty acids, carboxylic amides; monoalkanolamine condensates and polyoxyethylene fatty acid amides.

5. The method of claim 4 wherein the non-ionic surfactant is 2-[4-(2,4,4-trimethylpentan-2-yl)phenoxy]ethanol.

6. The method of claim 1, wherein the reducing agent is in an amount to break disulphide bonds and selected from the group consisting of β-mercaptoethanol, dithiothreitol, or tris (2-carboxyethyl) phosphine.

7. The method of claim 6, wherein the reducing agent is β-mercaptoethanol.

8. The method of claim 7, wherein β-mercaptoethanol is in an amount of 100 mM to 150 mM.

9. The method of claim 1, wherein the endoglycosidase is PNGaseF which has the ability to cleave N-linked glycans from glycoproteins when the innermost residue is GlcNAc.

10. The method of claim 1, wherein the released glycans are separated by liquid chromatography.

11. The method of claim 1, wherein the glycoprotein is an antibody, fragment thereof or fusion protein with multiple glycan sites.

12. The method of claim 1, wherein the method further comprises the steps of:

optionally adding an exoglycosidase in an amount of 0.1 units per 1 mg of denatured glycoprotein after step (e) or after step (g), and incubating the components at 37° C. for 30 minutes to provide a de-sialylated protein.

13. The method of claim 12, wherein the exoglycosidase is sialidase which has the ability to cleave terminal sialic acid from both N- and O-linked glycans of glycoproteins.

14. A method of partial de-glycosylation of a glycoprotein for comparing tertiary structure, wherein, the method comprising steps of:
(a) providing a glycoprotein;
(b) combining the glycoprotein with endoglycosidase to partially cleave N-linked glycans in an amount from 1 unit to 10 units per 1 mg of glycoprotein;
(c) incubating components of step (b) at 37° C. for 45 minutes to 8 hours to provide for a partially de-glycosylated protein.

15. The method of claim 14 wherein the endoglycosidase is PNGaseF which has the ability to cleave N-linked glycans from glycoproteins when the innermost residue is GlcNAc.

16. The method of claim 14, wherein the partially de-glycosylated glycoprotein is analysed using capillary electrophoresis.

17. The method of claim 14, wherein the glycoprotein is an antibody, fragment thereof or fusion protein with multiple glycan sites.

* * * * *